United States Patent [19]

Martin et al.

[11] 4,313,959

[45] Feb. 2, 1982

[54] (ARYLMETHYL)PHENYL-AMINOCY-CLOHEXANOLS, CYCLOHEXENES AND INTERMEDIATES THEREOF

[75] Inventors: Lawrence L. Martin, Lebanon, N.J.; Manfred Worm, Wiesbaden-Naurod, Fed. Rep. of Germany

[73] Assignee: Hoechst-Roussel Pharmaceuticals Inc., Somerville, N.J.

[21] Appl. No.: 258,097

[22] Filed: Apr. 27, 1981

[51] Int. Cl.$^3$ .................. A61K 31/315; C07C 91/16; C07C 87/36
[52] U.S. Cl. .......................... 424/330; 260/340.9 R; 564/265; 564/300; 564/307; 568/322; 568/329
[58] Field of Search ................ 564/315, 307; 424/330

[56] References Cited

U.S. PATENT DOCUMENTS

| | | | |
|---|---|---|---|
| 3,652,769 | 3/1972 | Saari | 564/307 |
| 4,028,415 | 6/1977 | Clark | 424/330 |

OTHER PUBLICATIONS

Lednicer et al., J. of Medicinal Chemistry, vol. 15, No. 12, 1235–1238, (1972).
Lednicer et al., J. of Medicinal Chemistry, vol. 15, No. 12, 1239–1243, (1972).
Carmalm et al., Chem. Absts., 83, 157704(a), 1975.
Carenini et al., Chem. Absts., 80, 47509(q), 1974.

*Primary Examiner*—G. T. Breitenstein
*Attorney, Agent, or Firm*—Jerome Rosenstock

[57] ABSTRACT

(Arylmethyl)phenyl-aminocyclohexanols, (arylmethyl)phenyl aminocyclohexenes and (arylmethyl)phenyl-aminocyclohexanes and methods of preparing same are described. These compounds are useful as antidepressants and anticonvulsants.

Compounds 8-[2-(phenylmethyl)phenyl]-1,4-dioxaspiro[4,5]-decan-8-ol, 1-[2-(phenylmethyl)phenyl]-4-oxocyclohexanol, and 1-[2-(phenylmethyl)phenyl]-4-oxocyclohexanol oxime, and methods of preparing same are also described. These compounds are useful as intermediates for preparing the antidepressant and anticonvulsant compounds.

20 Claims, No Drawings

(ARYLMETHYL)PHENYL-AMINOCYCLOHEX- ANOLS, CYCLOHEXENES AND INTERMEDIATES THEREOF

This invention relates to (arylmethyl)phenyl-amino- cyclohexanes of the general formula

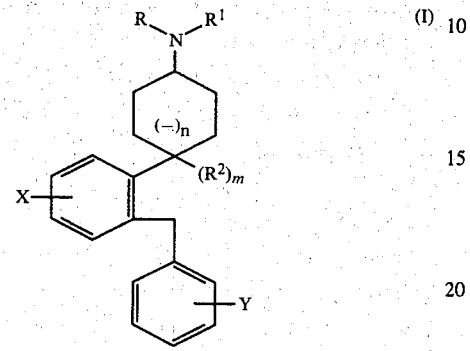

which are useful as antidepressants and anticonvulsants, wherein each of R and $R^1$ is hydrogen or lower alkyl, $R^2$ is hydrogen or hydroxyl; m is an integer of 0 or 1; n is an integer of 0 or 1 and when m is 0, n is 1 and the compound is a cyclohexene derivative; when m is 1, n is 0 and the compound is a cyclohexane derivative; and each of X and Y is hydrogen, halogen, alkoxy of 1 or 2 carbon atoms, lower alkyl, hydroxy and trifluoromethyl; to methods of synthesizing said compounds; to methods of treatment with pharmaceutically effective amounts thereof; and to pharmaceutical compositions containing such compounds as active ingredients.

This invention relates to 8-[2-phenylmethyl)phenyl]- 1,4-dioxaspiro(4.5)decan-8-ol, 1-[2-(phenylmethyl)- phenyl]-4-oxocyclo-hexanol, and 1-[2-(phenylmethyl)- phenyl]-4-oxocyclohexanol oxime which are useful as intermediates for synthesizing the aforementioned (aryl- methyl)phenyl-aminocyclohexanes, and to methods of synthesizing them.

The term "lower alkyl" as used throughout the specification and appended claims refers to a straight or branched alkyl group having up to 6 carbon atoms.

When m is 1, (n is 0) the compounds of the present invention encompass both cis and trans structural isomers. The cis structural isomer is as shown in formula I(a) below:

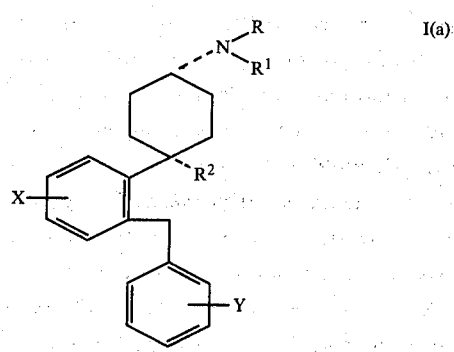

The trans structural isomer is as shown in formula I(b) below:

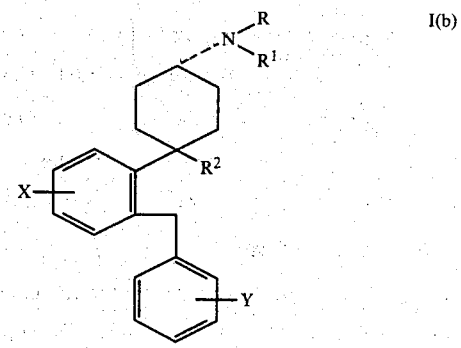

To the best of our knowledge, the compounds of this invention have not heretofore been made, used, described or suggested.

The (arylmethyl)phenyl-aminocyclohexanols of the general formula

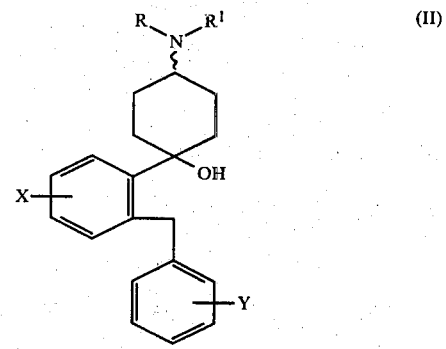

wherein R, $R^1$, X and Y are as mentioned earlier are synthesized in the following manner:

A 2-bromodiphenylmethane of the formula

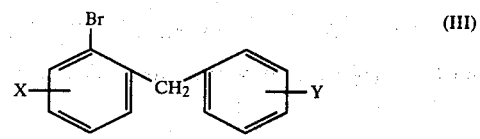

in which X and Y are as previously defined is converted to a corresponding organometallic derivative thereof in a conventional manner e.g., to its lithio derivative by treatment with an alkylithium at a temperature of about −8° to −20° C. in a solvent such as ether, hexane or tetrahydrofuran. The resulting organometallic derivative, e.g. lithio derivative, is allowed to react with a compound of the formula

where R and $R^1$ are as previously defined, at a temperature of −80° to −20° C., preferably −60° to −30° C. in a solvent such as ether, tetrahydrofuran or hexane to provide the compound of formula (II).

The starting 2-bromodiphenylmethane of formula (III) is prepared by reducing a corresponding 2-bromobenzophenone. One suitable method of carrying out this reduction is via Clemmensen reduction. Another very suitable method involves the use of hydroiodic acid and red phosphorus under reflux conditions. One suitable method of preparing the 2-bromobenzophenone is by reacting a 2-bromobenzoyl chloride of the formula

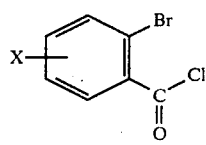

with a benzene of the formula

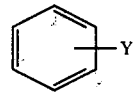

under Friedel-Crafts conditions (X and Y in the above formula are as defined above).

The (arylmethyl)phenyl-aminocyclohexanol of formula (II) described above is dehydrated to its corresponding (arylmethyl)phenyl-aminocyclohexene of the formula

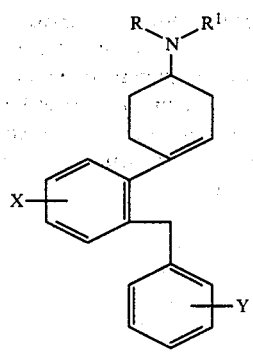

The dehydration can be carried out with one of several dehydrating agents including trifluoroacetic acid, formic acid and a mixture of glacial acetic and concentrated hydrochloric acid, the reaction temperature being from the ambient to the reflux temperature of the reaction mixture.

(Arylmethyl)phenyl-aminocyclohexanes corresponding to $R^2 = H$ in formula (I) can be obtained by hydrogenating the above-described (arylmethyl)phenyl-aminocyclohexene of formula (IV) in any suitable manner known in the art.

The compounds of this invention, 8-[2-(phenylmethyl)phenyl]-1,4-dioxaspiro(4.5)decan-8-ols (formula V), 1-[2-phenylmethyl)phenyl-4-oxocyclohexanols (formula VI), and 1-[2-(phenylmethyl)phenyl]-4-oxocyclohexanol oximes (formula VII) which are useful as intermediates for synthesizing the afore-mentioned (arylmethyl)phenyl-aminocyclohexanes can be synthesized in the following manner (referring to the schematic sequence below):

A corresponding 2-bromodiphenylmethane is converted to its organo-metallic derivative, e.g. its lithio derivative in the manner described earlier, and the resulting organo-metallic, e.g. lithio derivative, is allowed to react with 1,4-dioxaspiro(4.5)decan-8-one (formula VIII) at a temperature of $-80°$ to $-20°$ C., preferably $-60°$ to $-30°$ C. in a solvent such as ether, tetrahydrofuran or hexane to obtain the compound V. It is then subjected to conventional hydrolysis by a method known to the art to provide the compound VI. One such method is carried out with a refluxing mixture of methanol and an equimolar quantity of hydrochloric acid. The compound VI is then converted to the oxime of formula VII by a suitable conventional method known to the art, e.g. by reaction with hydroxylamine hydrochloride.

The oxime compound VII is converted to a 1-[2-(phenylmethyl)phenyl]-4-aminocyclohexanol compound of formula II by suitable methods known to the art. For instance, the primary amine compound corresponding to R, $R^1$=hydrogen in formula II can be obtained by reducing the oxime VII by any suitable method known to the art, e.g. reduction with sodium bis(2-methoxyethoxy)aluminum hydride or with LiAlH$_4$. A monoalkylamino compound corresponding to R=H and $R^1$=alkyl is prepared by acylation of the primary amine with carboxylic acid anhydrides or chlorides or with chloroformate esters to afford the corresponding amides and carbamate derivatives which are reduced to secondary amines with LiAlH$_4$. A dialkylamino compound corresponding to R and $R^1$=alkyl can be obtained by alkylating the primary amine twice with an alkyl halide.

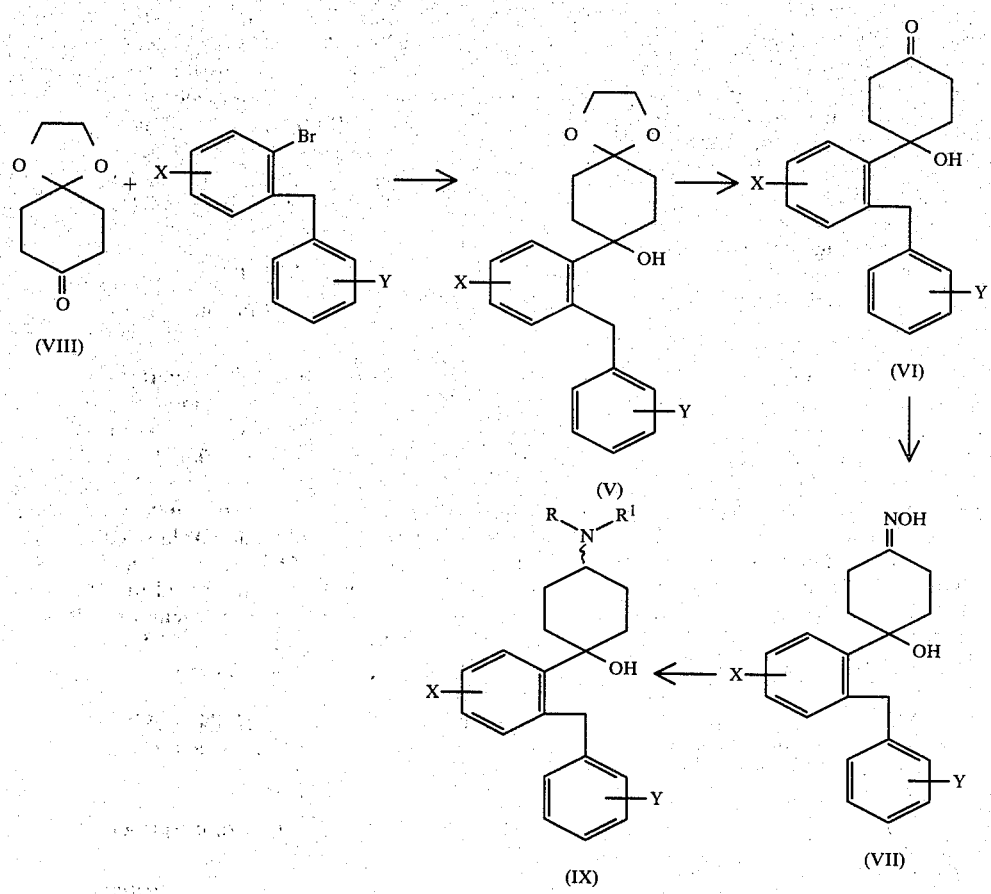

The compounds of the present invention of formula (I) are useful in the treatment of depression in mammals, as demonstrated by their ability to inhibit tetrabenazine-induced depression in mice (International Journal of Neuropharmacology, 8, 73 (1969), a standard assay for useful antidepressant properties. Thus, for instance, intraperitoneal doses of 4.7 mg/kg body weight of 1-[2-(phenylmethyl)phenyl]-4-dimethylaminocyclohexanol and 20 mg/kg of 1-[2-(phenylmethyl)phenyl]-4-dimethylaminocyclohex-1-ene effect, respectively, 50% and 30% inhibition of the ptosis of the tetrabenazine-induced depression in mice. These data illustrate that the compounds are useful as antidepressants in mammals when administered in amounts ranging from 1 to 50mg/kg of body weight per day.

Compounds of the presents invention of formula (I) are further useful as anticonvulsant agents for mammals, as determined by the method of Woodbury, L. A. and Davenport, V. D. (Arch. Int. Pharmacodynam, 92, pp. 97-107 (1952). For example, the intraperitoneal doses of 33.3 mg/kg of body weight of 1-[2-(phenylmethyl)-phenyl]-4-dimethylaminocyclohex-1-ene and 50.0 mg/kg of body weight of 1-[2-(phenylmethyl)phenyl]-4-dimethyl-aminocyclohex-1-ene effect, respectively, 50% and 30% protection from the effect of supramaximal electroshock. These data illustrate that compounds of this invention are useful in treating convulsions in mammals when administered in amounts ranging from 10 to 70 mg/kg of body weight per day.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. The preparations should contain at least 0.5% of active compound, but may be varied depending upon the particular form and may conveniently be between 4% to about 70% of the weight of the unit. The amount of active compound in such compositions is such that a suitable dosage wil be obtained. Preferred compositions and preparations according to the present invention are prepared so that an oral dosage unit form contains 1.0 to 300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin; and a flavoring agent such as peppermint, methyl salicylate, or orange flavoring. When the dosage unit is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain a pharmaceutically effective amount, i.e., at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The invention is illustrated by the following examples.

EXAMPLE 1

1-[2-(Phenylmethyl)phenyl]-4-dimethylaminocyclohexanol

To 24.7 g of 2-bromodiphenylmethane and 100 ml of dry tetrahydrofuran (THF, hereinafter) is added 55 ml of 2.4 molar solution of n-butyllithium in hexane dropwise with stirring at −40° to 50° C. under a dry nitrogen atmosphere. The resultant solution is stirred one hour after addition of the n-butyllithium is completed. A solution of 15.5 g 4-dimethylaminocyclohexanone in 50 ml of dry THF is added dropwise with stirring while maintaining the temperature below −40° C. The resultant solution is stirred at −40°0 to −50° C. for two hours after addition of the ketone is completed and further stirred under $N_2$ atmosphere overnight (16 hours) at room temperature. The solution is cooled to 0° C. and 350 ml of water and 400 ml of hexane are added thereto. The aqueous phase of the resultant mixture is removed and the product crystallized out of the organic phase. After filtration (washing the filter cake with hexane) the organic phase is washed three times with 100 ml portions of water and cooled overnight. A second crop is obtained, combined with the first crop and recrystallized from 50 ml of toluene to yield 9.46 g (30.6% yield) of 1-[2-(phenylmethyl)phenyl]-4-dimethylaminocyclohexanol, m.p. 140°–141° C.

Analysis: Calculated for $C_{21}H_{27}NO$: 81.51% C, 8.79% H, 4.53% N; Found: 81.38% C, 8.74% H, 4.45% N.

EXAMPLE 2

1-[2-(Phenylmethyl)phenyl]-4-dimethylaminocyclohex-1-ene

A solution of 7.0 g of 1-[2-(phenylmethyl)phenyl]-4-dimethylaminocyclohexanol of Example 1 in 30 ml of acetic acid and 3 ml of hydrochloric acid (concentrated) is heated to reflux for $4\frac{1}{2}$ hours. After the contents are allowed to stand at 5° C. for 3 days, the solvent is evaporated off and the residue is dissolved in 50 ml of water. The solution is filtered and made alkaline with a slight excess of 50% aqueous NaOH. After cooling, the product is collected by suction filtration, and the filter cake is washed with water and dried in vacuo over $P_2O_5$ at 40° C. to yield 6.57 g (99.7% yield) of 1-[2-(phenylmethyl)phenyl]-4-dimethylaminocyclohex-1-ene m.p. 44°–45° C.

Analysis: Calculated for $C_{21}H_{25}N$: 86.55% C, 8.65% H, 4.81% N; Found: 86.78% C, 8.68% H, 4.80% N.

EXAMPLE 3

8-[2-(Phenylmethyl)phenyl]-1,4-dioxaspiro(4.5)decan-8-ol 26.25 ml of 2.4 molar solution of n-butyllithium in n-hexane is added dropwise with stirring at −50° to −40° C. under dry nitrogen to a solution of 10.87 g of 2-bromodiphenylmethane in 25 ml of dry THF. The mixture is stirred at −50° to −40° C. for one hour after addition is completed. A solution of 6.30 g of 1,4-dioxaspiro(4.5)decan-8-one in 20 ml of dry THF is added dropwise at −50° to −40° C. This mixture is stirred overnight (16 hours) at −70° C. to +10° C., and quenched with 50 ml of water. The organic phase is diluted with 100 ml of ether and washed three times with 50 ml portions of water. The aqueous phase and the washing water are extracted with 100 ml of $CH_2Cl_2$, which is washed twice with 50 ml portions of water. The combined organic phases are dried over $Na_2SO_4$ and evaporated to an oil. This oil is treated with ether/hexane (20 ml/50 ml) mixture to give 6.0 g (45.8%) yield of crystalline product which is recrystallized from ether/hexane (10 ml/40 ml) to provide 5.53 g (42.2% yield) of 8-[2-(phenylmethyl)phenyl]-1,4-dioxaspiro(4.5)decan-8-ol, m.p. 97°–98° C.

Analysis: Calculated for $C_{21}H_{24}O_3$: 77.75% C, 7.46% H; Found: 77.49% C, 7.37% H.

EXAMPLE 4

1-[2-(Phenylmethyl)phenyl]-4-oxocyclohexanol

To a solution of 4.22 g of 8-[2-(phenylmethyl)phenyl]-1,4-dioxaspiro[4.5]decan-8-ol of Example 3 in 120 ml of methanol is added 10 ml of 5% HCl, and the mixture is stirred at room temperature for $3\frac{1}{2}$ hours. The solvent is removed under reduced pressure, and 200 ml of water and 10 ml of 5% NaOH are added. The product is collected, washed with water and dried over $P_2O_5$ and then recrystallized from 35 ml of methanol to give 2.40 g (64.9% yield) of 1-[2-(phenylmethyl)-phenyl]-4-oxocyclohexanol, m.p. 138.5°–139.5° C.

Elemental Analysis: Calculated for $C_{19}H_{20}O_2$: 81.40% C, 7.19% H; Found: 81.60% C, 7.19% H.

EXAMPLE 5

1-[2-(Phenylmethyl)phenyl]-4-oxocyclohexanol oxime

To a solution of 2.00 g of 1-[2-(phenylmethyl)-phenyl]-4-oxocyclohexanol of Example 4 in 100 ml of 95% ethanol is added a solution of 1.2 g of sodium acetate in 10 ml of $H_2O$ and a solution of 1.0 g of hydroxylamine hydrochloride in 4 ml of $H_2O$ and the mixture is refluxed for 90 minutes. The solvents are removed under reduced pressure and the product is crystallized from ethanol-$H_2O$ (20 ml–100 ml) and dried ($P_2O_5$—40°) in vacuo to provide 1.96 g of 1-[2-(phenyl-methyl)phenyl]-4-oxocyclohexanol oxime, m.p. 137°–138° C.

Elemental Analysis: Calculated for $C_{19}H_{21}NO_2$: 77.26% C, 7.17% H, 4.74% N; Found: 77.54% C, 7.10% H, 4.64% N.

This resulting compound of Example 5 can be reduced as described above, e.g. by reaction with sodium bis(2-methoxyethoxy)aluminum hydride or $LiAlH_4$ to yield a compound of the present invention, 1-[2-(phenylmethyl)phenyl]-4-aminocyclohexanol. This compound can be reacted as described above, with an alkyl halide, e.g. methyl iodide, to yield a compound of the present invention, e.g. 1-[2-(phenylmethyl)phenyl]-4-dimethylaminocyclohexanol.

We claim:

1. A compound of the formula

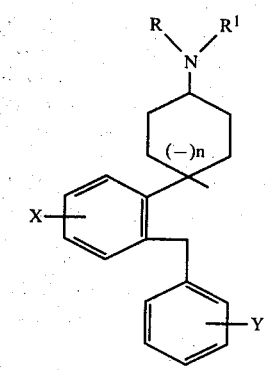

wherein R and $R^1$ are each independently hydrogen and lower alkyl, $R^2$ is hydrogen and hydroxyl; m is an integer of 0 or 1; n is an integer of 0 or 1; and when m is 1, n is 0 ; and when m is 0 , n is 1; and X and Y are each independently hydrogen, halogen, alkoxyl of 1 or 2 carbon atoms, lower alkyl, hydroxy and trifluoromethyl; and the stereoisomers thereof and a pharmaceutically acceptable acid addition salt of any of the foregoing.

2. A compound as defined in claim 1 wherein X is selected from hydrogen, fluorine, methyl and methoxy.

3. A compound as defined in claim 1 wherein Y is selected from hydrogen, fluorine, methyl or methoxy.

4. A compound as defined in claim 1 wherein R and $R^1$ are both hydrogen.

5. A compound as defined in claim 1 wherein R and $R^1$ are both methyl.

6. A compound as defined in claim 1 wherein R is hydrogen and $R^1$ is methyl.

7. A compound as defined in claim 1 wherein m is 1.

8. The cis isomer of the compound defined in claim 7.

9. The trans isomer of the compound defined in claim 7.

10. The compound as defined in claim 1 which is cis or trans 1-[2-(phenylmethyl)phenyl]-4-dimethylaminocyclohexanol or a salt thereof.

11. The compound as defined in claim 1 which is 1-[2-(phenylmethyl)phenyl]-4-dimethylaminocyclohex-1-ene, or a salt thereof.

12. The compound as defined in claim 1 which is cis or trans 1-[2-(phenylmethyl)phenyl]-4-dimethylaminocyclohexane or a salt thereof.

13. A method of treatment which comprises administering to a depressed patient a pharmaceutically effective amount of a compound defined in claim 1.

14. A method of treatment which comprises administering to a patient in need of preventing convulsion a pharmaceutically effective amount of a compound defined in claim 1.

15. A method of treatment which comprises administering to a depressed patient a pharmaceutically effective amount of a compound defined in claim 10 or claim 11 or claim 12.

16. A method of treatment which comprises administering to a patient in need of preventing convulsion a pharmaceutically effective amount of a compound defined in claim 10 or claim 11 or claim 12.

17. An antidepressant or anticonvulsant pharmaceutical composition which comprises an effective amount of a compound defined in claim 1 and a pharmaceutically acceptable carrier thereof.

18. The composition as defined in claim 17 which comprises between 0.5 and about 70% by weight of said compound.

19. An antidepressant or anticonvulsant pharmaceutical composition which comprises an effective amount of a compound defined in claim 10 or claim 11 or claim 12 and a pharmaceutically acceptable carrier thereof.

20. The composition as defined in claim 19 which comprises between 0.5 and about 70% by weight of said compound.

* * * * *

UNITED STATES PATENT AND TRADEMARK OFFICE
CERTIFICATE OF CORRECTION

PATENT NO. : 4,313,959
DATED : 2/2/82
INVENTOR(S) : Lawrence L. Martin, et al.

It is certified that error appears in the above—identified patent and that said Letters Patent is hereby corrected as shown below:

Column 2, line 53: "$-8°$" should be -- $-80°$ --

" 3, " 67: "glacial acetic" should be --glacial acetic acid--

" 5, " 51: "presents" should be --present--

" 7, " 61: "$-40°0$" should be -- $-40°$ --

" 8, " 2: "$100°ml$" should be --100 ml--

UNITED STATES PATENT AND TRADEMARK OFFICE
CERTIFICATE OF CORRECTION

PATENT NO. : 4,313,959

DATED : 2/2/82

INVENTOR(S) : Lawrence L. Martin, et al.

It is certified that error appears in the above—identified patent and that said Letters Patent is hereby corrected as shown below:

Claim 1, 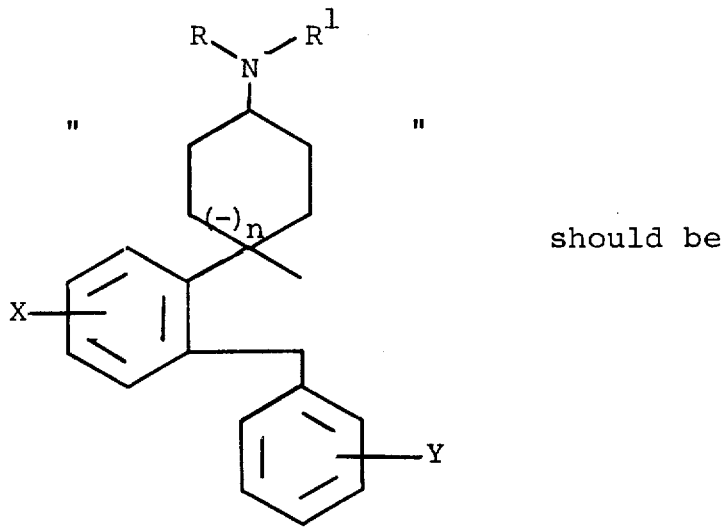 should be

UNITED STATES PATENT AND TRADEMARK OFFICE
CERTIFICATE OF CORRECTION

PATENT NO. : 4,313,959
DATED : 2/2/82
INVENTOR(S) : Lawrence L. Martin, et al.

It is certified that error appears in the above—identified patent and that said Letters Patent is hereby corrected as shown below:

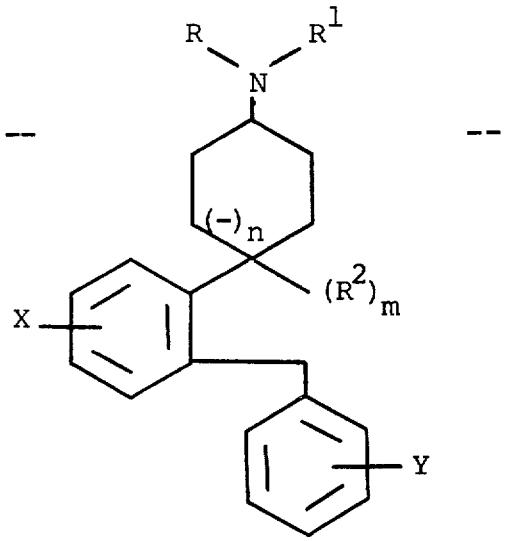

Signed and Sealed this

Twentieth Day of April 1982

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,313,959
DATED : February 2, 1982
INVENTOR(S) : Lawrence L. Martin and Manfred Worm It is certified that error appears in the above-identified patent and that said Letters Patent are hereby corrected as shown below:

Column 5, lines 56 and 57:

"1-[2-(phenylmethyl)phenyl]-4-dimethylaminocyclohex-1-ene"

should be

-- 1-[2-(phenylmethyl)phenyl]-4-dimethylaminocyclohexanol --

Signed and Sealed this

Third Day of August 1982

[SEAL]

Attest:

Attesting Officer

GERALD J. MOSSINGHOFF

*Commissioner of Patents and Trademarks*